United States Patent

Audousset et al.

Patent Number: 5,494,490
Date of Patent: Feb. 27, 1996

[54] OXIDATIVE DYEING COMPOSITIONS CONTAINING 4-HYDROXY OR 4-AMINOBENZIMIDAZOLE OR DERITIVES THEREOF AS COUPLERS, AND PROCESS FOR IMPLEMENTATION

[75] Inventors: Marie P. Audousset, Levallois-Perret; Jean Cotteret, Verneuil;-sur-Seine, both of France

[73] Assignee: L'Oreal, Paris, France

[21] Appl. No.: 155,177

[22] Filed: Nov. 19, 1993

[30] Foreign Application Priority Data

Nov. 20, 1992 [FR] France ................................. 9213999

[51] Int. Cl.$^6$ ..................................... A61K 7/13
[52] U.S. Cl. ................ 8/409; 8/406; 8/407; 8/408; 8/410; 8/412; 8/423
[58] Field of Search ................ 8/406, 407, 408, 8/409, 410, 423, 412

[56] References Cited

U.S. PATENT DOCUMENTS

| | | | |
|---|---|---|---|
| 3,658,455 | 4/1972 | Kalopissis et al. | 8/409 |
| 5,137,538 | 8/1992 | Mandrange et al. | 8/408 |
| 5,203,875 | 4/1993 | Tuloup et al. | 8/405 |

FOREIGN PATENT DOCUMENTS 0004368  10/1979  European Pat. Off. .
1921911   6/1968  Germany .

Primary Examiner—Paul Lieberman
Assistant Examiner—Caroline L. Dusheck
Attorney, Agent, or Firm—Jacobson, Price, Holman & Stern

[57] ABSTRACT

Processes for the dyeing of keratinous fibers with compositions which contain 4-hydroxy- or 4-aminobenzimidazole or their derivatives corresponding to the formula (I):

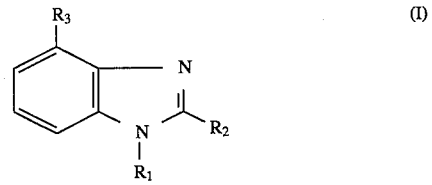

in which:

$R_1$ and $R_2$ represent hydrogen or alkyl, one at least of the substituents being equal to hydrogen, $R_3$ denotes OH or $NH_2$, as coupler for dyeing keratinous fibers, in particular hair, in the presence of a p-phenylenediamine, the ratio between the p-phenylenediamine and the coupler of formula (I) being greater than or equal to 1.2.

18 Claims, No Drawings

OXIDATIVE DYEING COMPOSITIONS CONTAINING 4-HYDROXY OR 4-AMINOBENZIMIDAZOLE OR DERITIVES THEREOF AS COUPLERS, AND PROCESS FOR IMPLEMENTATION

The present invention relates to the use of 4-hydroxy- or 4-aminobenzimidazole or their derivatives as couplers in the presence of oxidation dye precursors of paraphenylenediamine type in dyeing compositions for keratinous fibres and in particular for human hair, to the processes for implementation and to the compositions containing the coupler and at least one p-phenylenediamine.

It is known to dye keratinous fibres and in particular human hair with dyeing compositions containing oxidation dye precursors and in particular p-phenylenediamines or ortho- or paraaminophenols, generally called "oxidation bases".

It is also known that it is possible to obtain a colouring or to vary the shades obtained with these oxidation bases by combining them with couplers, also-called colouring modifiers, chosen in particular from aromatic metadiamines, metaaminophenols and metadiphenols.

The use has also already been envisaged, as coupler, of benzimidazole derivatives with oxidation dye precursors, the oxidation dye precursor or "base" and the coupler being used in a base/coupler ratio equal to or less than 1.

In the field of hair colouring, the search is for compositions which make it possible to confer on hair a colouring having satisfactory resistance to light, to washing, to bad weather and to perspiration.

The resistance to perspiration has a very specific significance, in as much as blue and ash-grey shades often have a tendency to redden under the effect of perspiration.

The Applicant has discovered, surprisingly, that by using certain benzimidazole derivatives with oxidation bases chosen from p-phenylenediamines and in an oxidation base/benzimidazole ratio equal to or greater than 1.2 and preferably equal to or greater than 1.5, it was possible to obtain colourings having a particularly notable tenacity to perspiration, while preserving good resistance to light and to washing.

The subject of the invention is thus the use of 4-hydroxy- or 4-aminobenzimidazole or their derivatives as couplers in dyeing compositions for keratinous fibres containing p-phenylenediamines in specific p-phenylenediamine/coupler ratios.

Another subject of the invention consists of the compositions containing 4-hydroxy- or 4-aminobenzimidazole or their derivatives and a p-phenylenediamine in these specific ratios.

Another subject of the invention is a dyeing process using 4-hydroxy- or 4-aminobenzimidazole or their derivatives in specific proportions with respect to the p-phenylenediamines.

Other subjects of the invention will become apparent on reading the description and examples which follow.

The subject of the invention is thus the use of a 4-hydroxy- or a 4-aminobenzimidazole or their derivatives, corresponding to the formula (I):

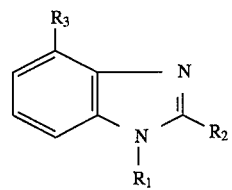

in which:

$R_1$ and $R_2$ represent hydrogen or alkyl, one at least of the substituents being equal to hydrogen;

$R_3$ denotes OH or $NH_2$, as couplers for the colouring of keratinous fibres, in combination with a p-phenylenediamine, in a p-phenylenediamine/coupler ratio equal to or greater than 1.2.

The alkyl radical for the compounds of formula (I) more particularly denotes lower alkyl having 1 to 4 carbon atoms, such as methyl, ethyl or propyl.

The paraphenylenediamines are chosen from the compounds corresponding to the formula (II) below:

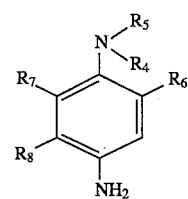

in which:

$R_6$, $R_7$ and $R_8$, which are identical or different, represent a hydrogen or halogen atom, an alkyl or hydroxyalkyl radical having 1 to 4 carbon atoms, an alkoxy radical having 1 to 4 carbon atoms or a carboxyl radical; $R_4$ and $R_5$, which are identical or different, represent a hydrogen atom or an alkyl, hydroxyalkyl, alkoxyalkyl, carbamoylalkyl, mesylaminoalkyl, acetylaminoalkyl, sulphoalkyl, ureidoalkyl, carbalkoxyaminoalkyl, piperidinoalkyl, morpholinoalkyl or phenyl radical, these alkyl or alkoxy groups having from 1 to 4 carbon atoms, or else $R_4$ and $R_5$ form, jointly with the nitrogen atom to which they are bonded, a piperidino or morpholino heterocycle, with the proviso that $R_7$ or $R_6$ represents a hydrogen atom when $R_4$ and $R_5$ do not represent a hydrogen atom, and the salts of these compounds.

Mention may be made, among the compounds of formula (II), of p-phenylenediamine, p-toluylenediamine, methoxyparaphenylenediamine, chloroparaphenylenediamine, 2,6-dimethylparaphenylenediamine, 2,6-diethylparaphenylenediamine, 2,5-dimethylparaphenylenediamine, 2-methyl-5-methoxyparaphenylenediamine, 2,6-dimethyl-5-methoxyparaphenylenediamine, N,N-dimethylparaphenylenediamine, N,N-diethylparaphenylenediamine, N,N-dipropylparaphenylenediamine, 3-methyl-4-amino-N,N-diethylaniline, N,N-di(β-hydroxyethyl)paraphenylenediamine, 3-methyl-4-amino-N, N-di(β-hydroxyethyl)aniline, 3-chloro- 4-amino-N,N-di(β-hydroxyethyl)aniline, 4-amino-N-ethyl-N-(carbamoylmethyl)aniline, 3-methyl-4-amino-N-ethyl-N-(carbamoylmethyl)aniline, 4-amino-N-ethyl-N-(β-piperidinoethyl)aniline, 3-methyl-4-amino-N-ethyl-N-(β-piperidinoethyl)aniline, 4-amino-N-ethyl-N-(β-morpholinoethyl)aniline, 3-methyl-4-amino-N-ethyl-N-(β-morpholinoethyl)aniline, 4-amino-N-ethyl-N-(β-acetylaminoethyl)aniline, 4-amino-N-(β-methoxyethyl)aniline, 3-methyl-4-amino-N-ethyl-N-(β-acetylaminoethyl)aniline, 4-amino-N-ethyl-N-(β -mesylaminoethyl)aniline, 3-methyl-4-amino-N-ethyl-N-(β -mesylaminoethyl)aniline, 4-amino-N-ethyl-N-(β-sulphoethyl)aniline, 3-methyl-4-amino-N-ethyl-N-(β-sulphoethyl)aniline, N-(4'-aminophenyl)morpholine, N-(4'-aminophenyl)piperidine, 2-hydroxyethylparaphenylenediamine, fluoroparaphenylenediamine, carboxyparaphenylenediamine, 2-isopropylparaphenylenediamine, 2-n-propylparaphenylenediamine, hydroxy-2-n-propylparaphenylenediamine or 2-hydroxymethylparaphenylenediamine.

These p-phenylenediamines can be introduced into the dyeing composition either in the free base form or in the salt form, such as in the hydrochloride, hydrobromide or sulphate form.

According to a preferred embodiment, 4-hydroxybenzimidazole, in combination with p-phenylenediamine or with p-toluylenediamine, is used.

In addition to the coupler of formula (I) and p-phenylenediamines, it is possible jointly to use other dye precursors of para and/or ortho type, chosen more particularly from the so-called "double" bases which are bisphenylalkylenediamines, para heterocyclic precursors such as 2,5-diaminopyridine, 2-hydroxy-5-aminopyridine or tetraaminopyrimidine, orthoaminophenols such as 1-amino-2-hydroxybenzene, 6-methyl-1-hydroxy-2-aminobenzene or 4-methyl-1-amino-2-hydroxybenzene and orthophenylenediamines.

The so-called double bases of the bisphenylalkylenediamine family correspond to the formula:

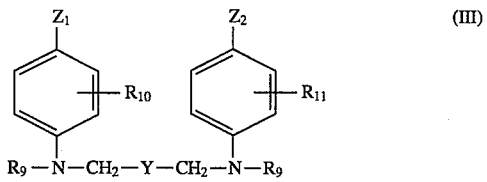

(III)

in which:

$Z_1$ and $Z_2$, which are identical or different, represent hydroxyl groups or $NHR_{12}$ groups where $R_{12}$ denotes a hydrogen atom or a lower alkyl radical;

$R_{10}$ and $R_{11}$, which are identical or different, represent either hydrogen atoms or halogen atoms or also alkyl groups;

$R_9$ represents a hydrogen atom or an alkyl, hydroxyalkyl or aminoalkyl group in which the amino residue may be substituted;

Y represents a radical taken from the group consisting of the following radicals: —$(CH_2)_n$—, $(CH_2)_m$—O—$(CH_2)_m$,

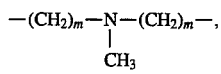

—$(CH_2)_m$—CHOH—$(CH_2)_m$;

n being an integer between 0 and 8 and m an integer between 0 and 4, it being possible for this base to be provided in the form of its addition salts with acids.

The alkyl or alkoxy radicals preferably denote a group having 1 to 4 carbon atoms and in particular methyl, ethyl, propyl, methoxy or ethoxy.

Mention may be made, among the compounds of formula (III), of N,N'-bis(β-hydroxyethyl)-N,N'-bis(4'-aminophenyl)- 1,3-diamino-2-propanol, N,N'-bis(β-hydroxyethyl)-N, N' -bis(4'-aminophenyl)ethylenediamine, N,N'-bis( 4-aminophenyl)tetramethylenediamine, N,N'-bis(β-hydroxyethyl)-N,N' -bis(4-aminophenyl)tetramethylenediamine, N,N'-bis(4-methylaminophenyl)tetramethylenediamine or N,N'-bis(ethyl)-N,N'-bis(4'-amino-3'-methylphenyl)ethylenediamine.

A preferred embodiment of the invention consists in using at least one paraphenylenediamine, optionally in combination with a so-called "double" base. 4-Hydroxybenzimidazole, in combination with p-phenylenediamine or with p-toluylenediamine and with N,N'-bis(β-hydroxyethyl)-N, N' -bis(4'-aminophenyl)-1,3-diamino-2-propanol, will more particularly be used.

In addition to 4-hydroxy- or 4-aminobenzimidazole or their derivatives, it is possible to jointly use other couplers known per se, such as metadiphenols, metaaminophenols, metaacylaminophenols, metaureidophenols, metacarbalkoxyaminophenols, naphthols, couplers having an active methylene group such as β-ketone compounds, pyrazolones or also the couplers of the indole family described more particularly in the following Patents: FR-A-2,636,236, EP-A-428,442, EP-A-428,441, EP-A-496,653 or EP-A-424, 261, and 4-hydroxyindole.

Particularly preferred couplers are chosen from metaaminophenol, 1,3-dihydroxy-4-chlorobenzene, 1,3-dihydroxybenzene, α-naphthol, 6-hydroxybenzomorpholine, 1-methyl-2-hydroxy-4-aminobenzene, 1-methyl-2-hydroxy-4-[(2-hydroxyethyl)amino]benzene, 1,3-dihydroxy-2-methylbenzene, 1-hydroxy-3,4-methylenedioxybenzene, 1-(β-hydroxyethylamino)- 3,4-methylenedioxybenzene, 2-bromo-4,5-methylenedioxyphenol, 2-amino-5-acetamidophenol, 6-hydroxyindole, 7-hydroxyindole, 7-aminoindole and 4-hydroxyindole.

It is also possible to use, jointly with the couplers of formula (I) and p-phenylenediamines, direct dyes well known in the state of the art, in particular for the purpose of shading or enriching colourings with highlights.

These direct dyes are chosen in particular from azo dyes, anthraquinone dyes or nitro derivatives of the benzene series.

The dyeing composition for keratinous fibres, in particular for human hair, which constitutes another subject of the invention, is essentially characterized in that it contains, in a medium suitable for dyeing keratinous fibres and cosmetically acceptable for hair, at least one compound corresponding to the abovementioned formula (I) and at least one p-phenylenediamine in proportions such that the p-phenylenediamine/coupler of formula (I) ratio is equal to or greater than 1.2 and preferably equal to or greater than 1.5.

The p-phenylenediamines are preferably chosen from those of the abovementioned formula (II), they may be combined with double bases and the composition may contain other couplers such as defined above and optionally direct dyes.

The coupler of formula (I) is present in the composition in proportions sufficient to develop, in oxidizing medium, a colouring with the p-phenylenediamine and preferably between 0.008 and 3.5% by weight with respect to the total weight of the composition and in particular between 0.05 and 2%.

The p-phenylenediamine is generally present in proportions of between 0.01 and 10% by weight with respect to the total weight of the composition and in particular between 0.05 and 4%.

The colouring of keratinous fibres and in particular of human hair is carried out by using the coupler of formula (I) and a p-phenylenediamine in the presence of an oxidizing agent. This oxidizing agent can be chosen from hydrogen peroxide, urea hydrogen peroxide, alkali metal bromates or persalts such as perborates and persulphates, hydrogen peroxide being particularly preferred.

The pH of the composition applied to keratinous fibres and in particular hair generally has a value between 3 and 11.

This pH can be adjusted by using acidifying or basifying agents well known in the field of dyeing keratinous fibres and in particular hair.

The dyeing compositions in accordance with the invention can also contain, in the preferred embodiment, anionic, cationic, non-ionic or amphoteric surface-active agents or their mixtures.

These surface-active agents are present in the compositions in accordance with the invention in proportions generally between 0.5 and 55% by weight and preferably between 2 and 50% by weight with respect to the total weight of the composition.

These compositions can also contain organic solvents for solubilizing the compounds which would not be sufficiently soluble in water. Mention may be made, among these solvents, by way of example, of lower $C_1$–$C_4$ alkanols such as ethanol and isopropanol, glycerol, glycols or glycol ethers such as 2-butoxyethanol, ethylene glycol, propylene glycol or the monoethyl ether and the monomethyl ether of diethylene glycol, and aromatic alcohols such as benzyl alcohol or phenoxyethanol and analogous products or their mixtures.

The solvents are preferably present in proportions between 1 and 40% by weight, and in particular between 5 and 30% by weight, with respect to the total weight of the composition.

The thickening agents which can be added to the compositions in accordance with the invention can be chosen from sodium alginate, gum arabic, cellulose derivatives, acrylic acid polymers, xanthan gum or scleroglucans. It is also possible to use inorganic thickening agents, such as bentonite.

These thickening agents are preferably present in proportions between 0.1 and 5%, and in particular between 0.2 and 3%, by weight with respect to the total weight of the composition.

The antioxidizing agents which can be present in the compositions are chosen in particular from sodium sulphite, thioglycolic acid, sodium bisulphite, dehydroascorbic acid, hydroquinone and homogentisic acid.

These antioxidizing agents are present in the composition in proportions between 0.05 and 1.5% by weight with respect to the total weight of the composition.

These compositions can also contain other cosmetically acceptable adjuvants such as, for example, penetration agents, sequestering agents, fragrances, buffers, and the like.

The compositions in accordance with the invention can be provided in various forms, such as in the liquid, cream or gel form or any other form suitable for carrying out dyeing of keratinous fibres and in particular of human hair. These compositions can be packaged in aerosol containers in the presence of a propellant.

The process for dyeing keratinous fibres, in particular hair, in accordance with the invention consists in applying to keratinous fibres a composition prepared at the time of use and containing at least one coupler of formula (I), at least one p-phenylenediamine in the p-phenylenediamine/coupler of formula (I) ratio defined above and at least one oxidizing agent in an amount sufficient to be able to develop a colouring.

According to a specific embodiment, a hydrogen peroxide solution in a concentration of 5 to 40 volumes is used. This solution is added to the dyeing composition and the mixture obtained is applied to the keratinous fibres. The fibres are left exposed for 5 to 40 minutes and preferably 15 to 30 minutes, after which the fibres are rinsed, washed with shampoo, rinsed again and dried.

According to another embodiment of the invention, there are separately applied a composition (A) containing, in a cosmetically acceptable medium, the coupler of formula (I) and a p-phenylenediamine in the ratio defined above to keratinous fibres and, after rinsing, a composition (B) containing the oxidizing agent.

It is also possible, in accordance with the invention, to apply separately a composition containing, in a cosmetically acceptable medium, a p-phenylenediamine, then, after rinsing, to apply a composition containing the coupler of formula (I) in a cosmetically acceptable medium and, in a last stage, the oxidizing agent, the p-phenylenediamine and the coupler being applied in proportions such that the ratio on the keratinous fibres between the p-phenylenediamine and the coupler of formula (I) is greater than or equal to 1.2, preferably greater than or equal to 1.5.

Another embodiment consists in applying, in a first step, a composition containing a p-phenylenediamine and then, after rinsing, a composition (B) containing, in a cosmetically acceptable medium, the coupler of formula (I) and the oxidizing agent, the p-phenylenediamine and the coupler of formula (I) being used in the ratios defined above.

The examples which follow are intended to illustrate the invention without, however, any limiting nature being implied.

EXAMPLES 1 TO 5

Hair is dyed by applying, to grey hair containing 90% white hairs or to bleached hair, an extemporaneous mixture, weight for weight, of the colouring composition (A) and of the oxidizing composition (B) (28 g of the mixture per 3 g of hair).

This mixture is allowed to act for 30 minutes and the hair is then rinsed and shampooed. After drying, the hair is dyed the shade specified at the bottom of the table.

| in g | 1 | 2 | 3 | 4 | 5 |
|---|---|---|---|---|---|
| Colouring composition (A) | | | | | |
| 4-Hydroxybenzimidazole.HBr | 0.6 | 0.86 | 0.75 | 1.32 | 1.16 |
| 2,6-Dimethylparaphenylenediamine.2HCl | 0.8 | | | | |
| Paratoluylenediamine.2HCl | | 1.14 | 1 | 1.58 | 1.74 |
| Substrate 1 | x | | | | |
| Substrate 2 | | x | x | x | x |
| Water q.s. for | 100 | 100 | 100 | 100 | 100 |
| Base/coupler Ratio | 1.33 | 1.32 | 1.34 | 1.2 | 1.5 |
| Oxidizing composition (B) | | | | | |
| 20 volumes Hydrogen peroxide solution | | | | | |
| Phosphoric acid q.s. pH | 1–1.5 | 3 | 3 | 3 | 3 |
| Shades obtained: | | | | | |
| on natural grey hair containing 90% white hairs | intense blue | blue | blue | — | — |
| on bleached hair | — | — | — | black | black |

| COLOURING SUBSTRATE 1 | |
|---|---|
| Oleyl alcohol polyglycerolated with 2 mol of glycerol | 4 g |
| Oleyl alcohol polyglycerolated with 4 mol | 5.7 g AM |

-continued

| | |
|---|---|
| of glycerol containing 78% AM | |
| Oleic acid | 3 g |
| Oleyl amine 2 EO, sold under the name "Ethomeen O 12" by the company Akzo | 7 g |
| Diethylaminopropyl laurylamino succinamate, sodium salt containing 55% AM | 3 g AM |
| Oleyl alcohol | 5 g |
| Oleic acid diethanolamide | 12 g |
| Propylene glycol | 3.5 g |
| Ethyl alcohol | 7 g |
| Dipropylene glycol | 0.5 g |
| Monomethyl ether of propylene glycol | 9 g |
| Sodium metabisulphite as an aqueous solution containing 35% AM | 0.46 g AM |
| Ammonium acetate | 0.8 g |
| Antioxidizing agent, sequestering agent q.s. | |
| Monoethanolamine q.s. pH = 9.8 | |

COLOURING SUBSTRATE 2

| | |
|---|---|
| Ammonium lauryl sulphate containing 30% AM | 6 g AM |
| Sodium metabisulphite as an aqueous solution containing 35% AM | 0.35 g AM |
| Ammonia as an aqueous solution containing 20% AM | 2 g AM |
| Sequestering agent q.s. | |

| | |
|---|---|
| 4-Aminobenzimidazole | 1.16 g |
| Paratoluylenediamine | 1.74 g |
| Ammonium lauryl sulphate | 20 g |
| Trilon B | 0.3 g |
| 20% Aqueous ammonia | 10 g |
| 40% Sodium bisulphite | 1 g |
| Water | q.s. for 100 g |

The base/coupler ratio by weight is equal to 1.5.

At the time of use, this composition is mixed with an equal weight of 20 volumes hydrogen peroxide and is applied to locks of permanent wave grey hair.

After an exposure time of 30 minutes followed by rinsing, the hair is dyed brown.

EXAMPLE 7

| | |
|---|---|
| 4-Hydroxybenzimidazole hydrobromide | 0.66 g |
| Paratoluylenediamine | 0.79 g |
| Ammonium lauryl sulphate | 6 g |
| Ethylenediaminetetraacetic acid | 0.3 g |
| 20% Aqueous ammonia | 10 g |
| Sodium metabisulphite | 0.35 g |
| Water | q.s. for 100 g |

At the time of use, this composition is mixed, weight for weight, with a 20 volumes hydrogen peroxide solution.

The resulting composition, applied to grey hair containing 90% white hairs, for 30 minutes, confers on it, after rinsing and washing, a deep purple dark grey colouring.

We claim:

1. A process for dyeing keratinous fibres, in particular hair, comprising applying to the keratinous fibres as a coupler 4-hydroxy- or 4-aminobenzimidazole or their derivatives corresponding to the formula (I):

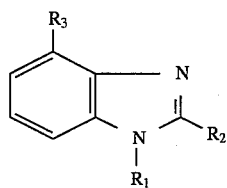

in which:

$R_1$ and $R_2$ represent hydrogen or alkyl, one at least of the substituents being equal to hydrogen;

$R_3$ denotes OH or $NH_2$, in the presence of a paraphenylenediamine, the weight ratio between the paraphenylenediamine and the coupler of formula (I) being greater than or equal to 1.2/1.

2. Process according to claim 1, wherein the paraphenylenediamine is selected from compounds corresponding to the formula (II):

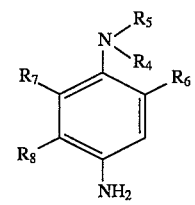

in which:

$R_6$, $R_7$ and $R_8$, which are identical or different, represent a hydrogen or halogen atom, an alkyl or hydroxyalkyl radical having 1 to 4 carbon atoms, an alkoxy radical having 1 to 4 carbon atoms or a carboxyl radical; $R_4$ and $R_5$, which are identical or different, represent a hydrogen atom or an alkyl, hydroxyalkyl, alkoxyalkyl, carbamoylalkyl, mesylaminoalkyl, acetylaminoalkyl, sulphoalkyl, ureidoalkyl, carbalkoxyaminoalkyl, piperidinoalkyl, morpholinoalkyl or phenyl radical, these alkyl or alkoxy groups having from 1 to 4 carbon atoms, or else $R_4$ and $R_5$ form, jointly with the nitrogen atom to which they are bonded, a piperidino or morpholino heterocycle, with the proviso that $R_6$ or $R_7$ represents a hydrogen atom when $R_4$ and $R_5$ do not represent a hydrogen atom, and the salts of these compounds.

3. Process according to claim 1, wherein 4-hydroxybenzimidazole is combined with p-phenylenediamine or with p-toluylenediamine.

4. Process according to claim 1, further comprising applying to the keratinous fibres other oxidation dye precursors selected from orthoaminophenols, orthophenylenediamines, bisphenylalkylenediamines or para heterocyclic precursors.

5. Process according to claim 4, comprising the bisphenylalkylenediamines selected from compounds corresponding to the formula (III):

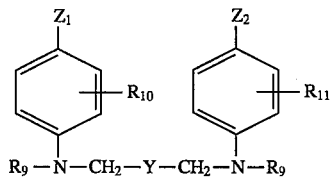

in which:

$Z_1$ and $Z_2$, which are identical or different, represent hydroxyl groups or $NHR_{12}$ groups where $R_{12}$ denotes a hydrogen atom or a lower alkyl radical;

$R_{10}$ and $R_{11}$, which are identical or different, represent hydrogen atoms, halogen atoms, or alkyl groups;

$R_9$ represents a hydrogen atom, an alkyl, hydroxyalkyl, or aminoalkyl group in which the amino residue may be substituted;

Y represents a radical selected from the group consisting of the following radicals: —$(CH_2)_n$—, $(CH_2)_m$—O—$(CH_2)_m$,

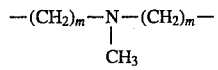

and —$(CH_2)_m$—CHOH—$(CH_2)_m$;

n being an integer between 0 and 8 and m an integer between 0 and 4, or its addition salts with acids.

6. Process according to claim 1 wherein 4-hydroxybenzimidazole is combined with p-phenylenediamine or with p-toluylenediamine and with N,N'-bis(β-hydroxyethyl)-N,N'-bis(4'-aminophenyl)- 1,3-diamino-2-propanol.

7. Process according to claim 1, further comprising, in addition to 4-hydroxy- or 4-aminobenzimidazole or their derivatives, other couplers selected from metadiphenols, metaaminophenols, metaacylaminophenols, metaureidophenols, metacarbalkoxyaminophenols, naphthols, couplers containing an active methylene group, pyrazolones and couplers of the indole family.

8. Dyeing composition for keratinous fibres, comprising in a medium suitable for dyeing keratinous fibres, at least one coupler of formula (I):

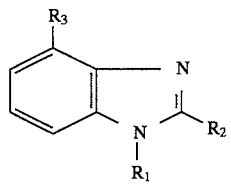

in which:

$R_1$ and $R_2$ represent hydrogen or alkyl, one at least of the substituents being equal to hydrogen;

$R_3$ denotes OH or $NH_2$, and at least one p-phenylenediamine, the weight ratio of the p-phenylenediamine and the coupler of formula (I) being greater than or equal to 1.2/1.

9. Composition according to claim 8, wherein the p-phenylenediamine is selected from compounds corresponding to the formula II:

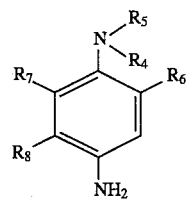

in which $R_6$, $R_7$ and $R_8$, which are identical or different, represent a hydrogen or halogen atom, an alkyl or hydroxyalkyl radical having 1 to 4 carbon atoms, an alkoxy radical having 1 to 4 carbon atoms or a carboxyl radical; $R_4$ and $R_5$, which are identical or different, represent a hydrogen atom or an alkyl, hydroxyalkyl, alkoxyalkyl, carbamoylalkyl, mesylaminoalkyl, acetylaminoalkyl, sulphoalkyl, ureidoalkyl, carbalkoxyaminoalkyl, piperidinoalkyl, morpholinoalkyl or phenyl radical, these alkyl or alkoxy groups having from 1 to 4 carbon atoms, or else $R_4$ and $R_5$ form, jointly with the nitrogen atom to which they are bonded, a piperidino or morpholino heterocycle, with the proviso that $R_4$ and $R_5$ do not represent a hydrogen atom, and the salts of these compounds.

10. Composition according to claim 8, further comprising couplers other than those of formula (I) or direct dyes.

11. Composition according to claim 8, wherein the coupler of formula (I) is present in proportions between 0.008 and 3.5% by weight with respect to the total weight of the composition.

12. Composition according to claim 8, wherein the p-phenylenediamine is present in the composition in proportions between 0.01 and 10% by weight with respect to the total weight of the composition, the p-phenylenediamine/coupler of formula (I) weight ratio being equal to or greater than 1.2/1.

13. Composition according to claim 12, wherein the p-phenylenediamine/coupler of formula (I) weight ratio is greater than or equal to 1.5/1.

14. Dyeing composition according to claim 8, wherein the p-phenylenediamine/coupler of formula (I) weight ratio is greater than or equal to 1.5/1.

15. Process for colouring keratinous fibres, comprising as a dyeing composition in a medium suitable for dyeing keratinous fibres, at least one coupler of formula (I):

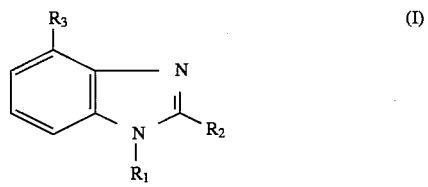

in which:

$R_1$ and $R_2$ represent hydrogen or alkyl, one at least of the substituents being equal to hydrogen;

$R_3$ denotes OH or $NH_2$, and at least one p-phenylenediamine, the weight ratio of the p-phenylenediamine and the coupler of formula (I) being greater than or equal to 1.2/1, said dyeing composition being mixed with an oxidizing agent and then applied to the keratinous fibres in amounts sufficient to develop the colouring during application to the keratinous fibres.

16. Process for colouring keratinous fibres, comprising applying to the keratinous fibres a composition (A) containing, in a medium suitable for dyeing, a coupler of formula (I):

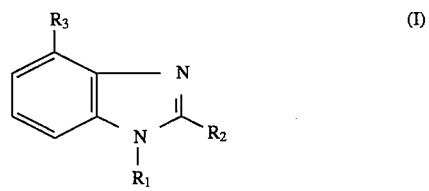

in which:

$R_1$ and $R_2$ represent hydrogen or alkyl, one at least of the substituents being equal to hydrogen;

$R_3$ denotes OH or $NH_2$, and a p-phenylenediamine, said coupler being present in proportions between 0.008 and 3.5% by weight with respect to the total weight of the composition, and, after rinsing, applying to the keratinous fibres a composition (B) containing an oxidizing agent, the weight ratio between the p-phenylenediamine and the coupler of formula (I) being greater than or equal to 1.2/1.

17. Process for dyeing keratinous fibres, comprising applying to the keratinous fibres, in a first step, a composition (A) containing a p-phenylenediamine in a medium suitable for dyeing and, after rinsing, applying to the keratinous fibres a composition (B) containing, in a medium suitable for dyeing, a coupler of formula (I):

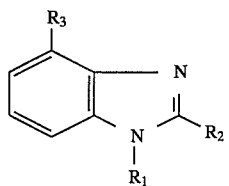

in which:

$R_1$ and $R_2$ represent hydrogen or alkyl, one at least of the substituents being equal to hydrogen;

$R_3$ denotes OH or $NH_2$, and an oxidizing agent, the said coupler being present in proportions such that the p-phenylenediamine/coupler of formula (I) weight ratio is greater than or equal to 1.2/1.

18. Process according to claim 17, wherein said p-phenylenediamine is present in proportions between 0.01 and 10% by weight with respect to the total weight of the composition.

* * * * *